(12) United States Patent
Giotis

(10) Patent No.: US 8,801,743 B2
(45) Date of Patent: Aug. 12, 2014

(54) HAIR TRANSPLANTING DEVICE AND METHOD FOR THE USE THEREOF

(76) Inventor: Konstantinos P. Giotis, Athens (GR)

( * ) Notice: Subject to any disclaimer, the term of this patent is extended or adjusted under 35 U.S.C. 154(b) by 713 days.

(21) Appl. No.: 12/803,361

(22) Filed: Jun. 25, 2010

(65) Prior Publication Data

US 2011/0319921 A1 Dec. 29, 2011
US 2013/0226212 A9 Aug. 29, 2013

Related U.S. Application Data

(63) Continuation of application No. PCT/GR2007/000065, filed on Dec. 27, 2007.

(51) Int. Cl.
*A61B 17/34* (2006.01)

(52) U.S. Cl.
USPC ........................................................ 606/187

(58) Field of Classification Search
USPC .................. 604/57, 59–63; 606/131, 133, 187
See application file for complete search history.

(56) References Cited

U.S. PATENT DOCUMENTS

| | | |
|---|---|---|
| 4,122,855 A | 10/1978 | Tezel |
| 5,817,120 A | 10/1998 | Rassman |
| 5,827,297 A | 10/1998 | Boudjema |
| 2003/0097144 A1 | 5/2003 | Lee |
| 2007/0038236 A1 | 2/2007 | Cohen |

FOREIGN PATENT DOCUMENTS

| | | |
|---|---|---|
| DE | 42 43 461 | 9/1994 |
| EP | 1 642 541 | 4/2006 |
| FR | 2 816 823 | 5/2002 |
| WO | WO 2005/109799 | 11/2005 |

*Primary Examiner* — Ashley Fishback
(74) *Attorney, Agent, or Firm* — Dowell & Dowell, P.C.

(57) ABSTRACT

A direct hair transplanting device enabling sequential harvesting of single hair follicles from a donor region and implantation of the same at a recipient zone of the scalp comprising a tubular housing (30) with a forwardly projecting tubular needle (2) with an outermost end being formed with a conical obliquely cut knife edge cutting surface. A hair follicle is extracted through rotation of the cutting surface of the needle around a selected hair follicle at the target donor region of the scalp and implantation of the same at a selected recipient locus of the scalp being effected through initiating a forward stroke of a push rod (7) slidable within the interior of tubular needle (2) to implant the hair follicle into the scalp. Appropriate regulation and fine adjustment of the depth of intrusion of needle (2) into the scalp is obtained through differentiated depth of screwing of an internally threaded tubular shaft (35) holding the needle around an externally threaded perimeter of a cylindrical member (34) detachably mounted onto the tubular housing (30).

5 Claims, 8 Drawing Sheets

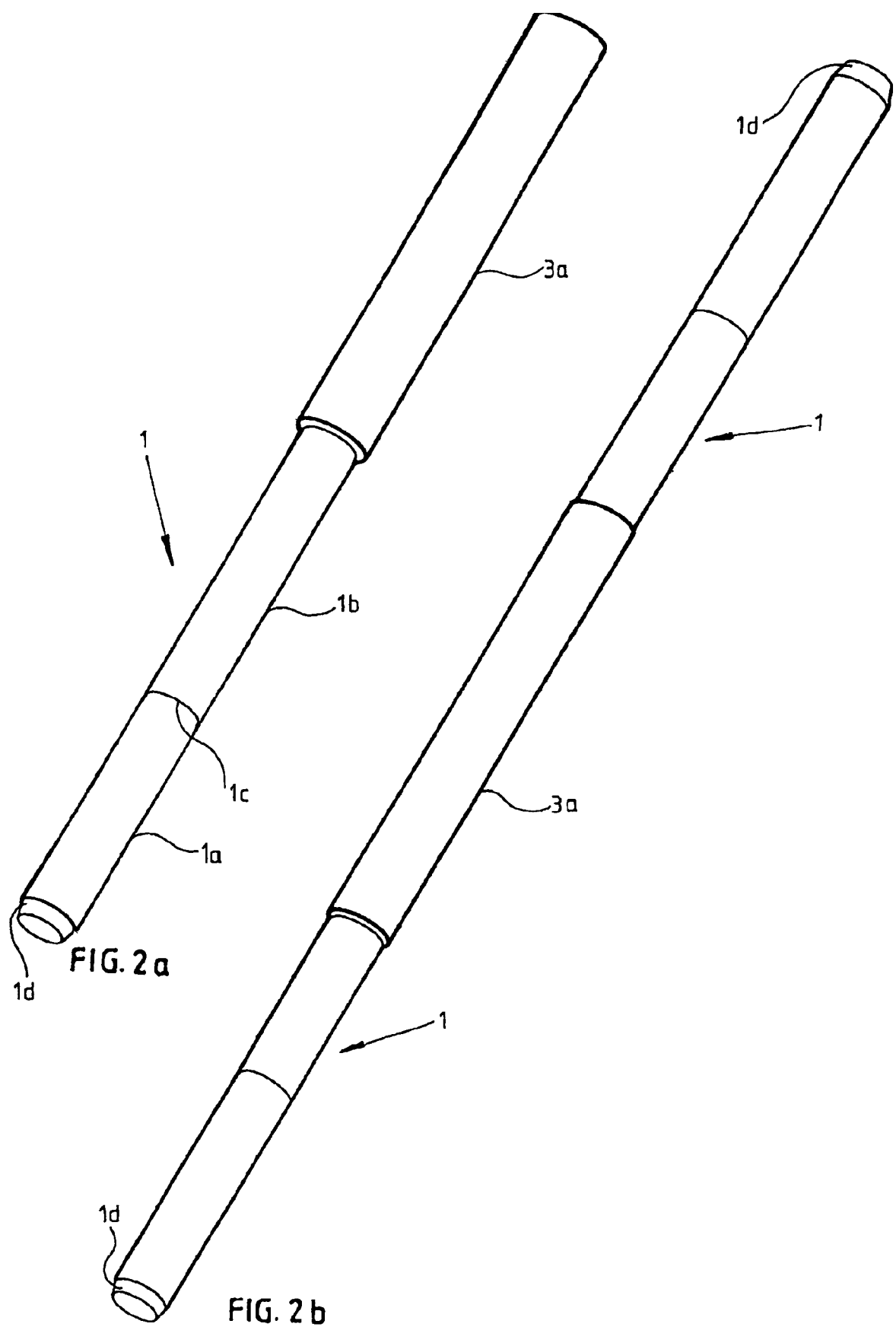

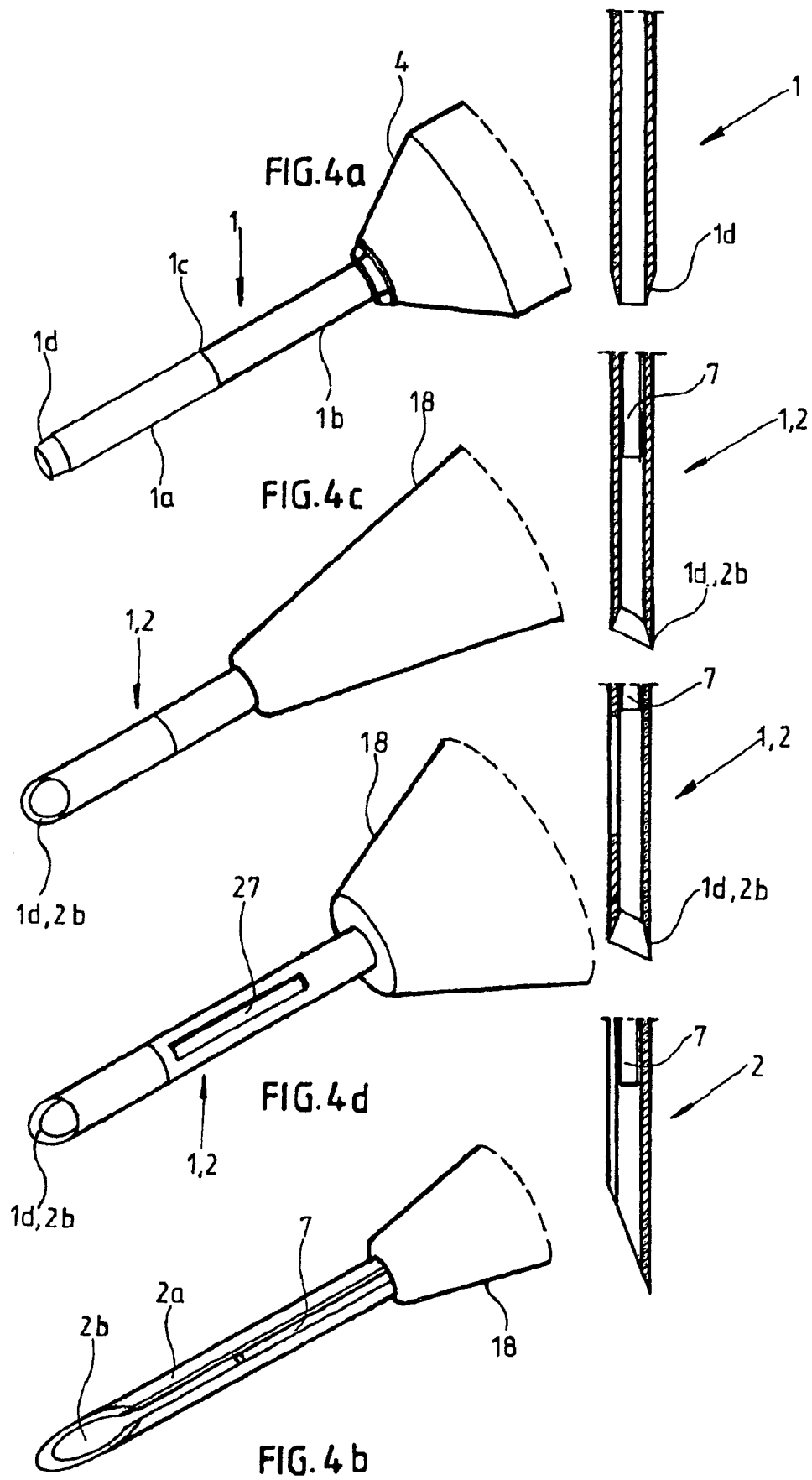

HAIR TRANSPLANTING DEVICE AND METHOD FOR THE USE THEREOF

THE FIELD OF THE ART

The invention relates to the direct hair implantation and in this respect it discloses appropriate transplanting equipment enabling sequential harvesting of single hair follicles from a donor region and implantation of the same at a recipient zone of the scalp.

THE BACKGROUND OF THE INVENTION

Various hair implantation procedures and equipment associated with the implementation thereof have been employed in the prior art. Follicular unit hair transplantation is the procedure most commonly used. This procedure is however invasive since it involves removal of a strip of the scalp from a donor area and placement of the graft at a recipient area. Such strip removal necessitates shaving and leaves a scar that is difficult to heal, thereby posing restrictions in the client's normal activities over a rather long healing period. The process is rather slow with short daily sessions enabling implantation of a limited number of hair of the order of 500 units, whilst its efficiency is rather low due to a large percentage of up to 20% of follicles being damaged during the removal of the strip and the subsequent division thereof in individual follicles to be implanted into the recipient zone. Eventually since a number of sessions must take place to perform the overall hair transplantation process and since such sessions have to be scheduled with extensively long intervals in between, it becomes uncomfortably long to complete the process. Furthermore, placement of hair follicles is subsequently performed by means of forceps thereby leaving much room for human error that often leads to oddly directioned hair at incorrect angles instead of the desired natural result of evenly angled hair. Moreover such graft extraction and subsequent implanting process is not available for all clients, e.g. very curly hair cannot be extracted, and a preliminary test has to be conducted to determine whether the process is suitable for each particular candidate.

The object of the present invention is to overcome and eliminate the abovementioned disadvantages and drawbacks of the prior art. With this scope in mind, the invention proposes a minimally invasive hair transplantation process that is available to all potential candidates without exception and requires neither shaving of the scalp nor removal of grafts or any preliminary testing whatsoever. Instead single hair follicles are extracted from a donor region to be subsequently implanted at a recipient region. The process is fast providing the possibility of an approximate number of 5,000 hair units being extracted in one session.

The object of the invention is further to disclose preferred specialized tools for the implementation of the abovementioned direct hair implantation process and in particular to propose alternative embodiments of tool devices as follows:

a. a hair harvesting device adapted to perform cutting of individual hair follicles comprising a tubular cutting head with a conical knife edge cutting surface formed at one end thereof or with conical knife edge cutting surfaces of different diameters formed at two ends thereof.
   b. a hair harvesting device comprising a cross like pattern of tubular cutting heads, each one being formed with a conical knife edge cutting surface of different diameter allowing removal of follicular hair units of varying diameters with a single harvesting instrument.
   c. a hair implanting device comprising a hollow needle having a longitudinal groove at a frontal portion thereof with an obliquely cut free end adapted to receive a follicular hair unit, a sliding rod being reciprocatingly movable axially along the needle to effect placement of the follicular hair unit disposed within the groove of the frontal end of the needle within a predetermined position of the scalp at the recipient bald area, and a tubular housing adapted to receive said needle and said sliding rod incorporating means of performing the hair implanting operation.

It is a further object of the invention to provide the aforementioned hair implanting device with means of appropriately regulating and fine adjustment of the depth of intrusion of the needle into the scalp to provide for optimum performance of the hair implanting device.

Another object of the invention is to disclose an electrically operated mode of the hair transplanting device.

A final object of the invention, in view of accelerating the hair transplantation process by avoiding the step of the tiresome exchange of instruments, is to provide a combined hair harvesting and hair implanting device operated preferably manually when effecting hair harvesting and preferably electrically when effecting hair implantation, wherein the aforementioned knife edge cutting surface of the hair harvesting device is obliquely cut so as to be adapted to perform the combined role of the follicular hair unit receiving groove of the hair implanting device.

BRIEF DESCRIPTION OF THE DRAWINGS

FIGS. 2a and 2b show a shank adapted to provide a handle means of the hair harvesting device respectively provided with a tubular cutting head at one end thereof or two tubular cutting heads of different diameters at two ends thereof.

FIG. 4a presents a detailed partial view of the hair harvesting device.

FIG. 4b presents a detailed partial view of the hair implanting device.

FIGS. 4c and 4d present in perspective a partial view of the cutting head of the hair harvesting device with an appropriately cut longitudinal groove at a frontal portion thereof and an obliquely cut frontal cutting edge so as to form a hair follicle receiving groove of the hair implanting device.

DETAILED DESCRIPTION OF PREFERRED EMBODIMENTS

The invention relates to equipment employed in a hair transplantation process in which individual hair follicles are extracted from a donor area of the scalp or from other hairy parts of the body to be subsequently individually implanted into a recipient bald area of the scalp.

Figure 1:
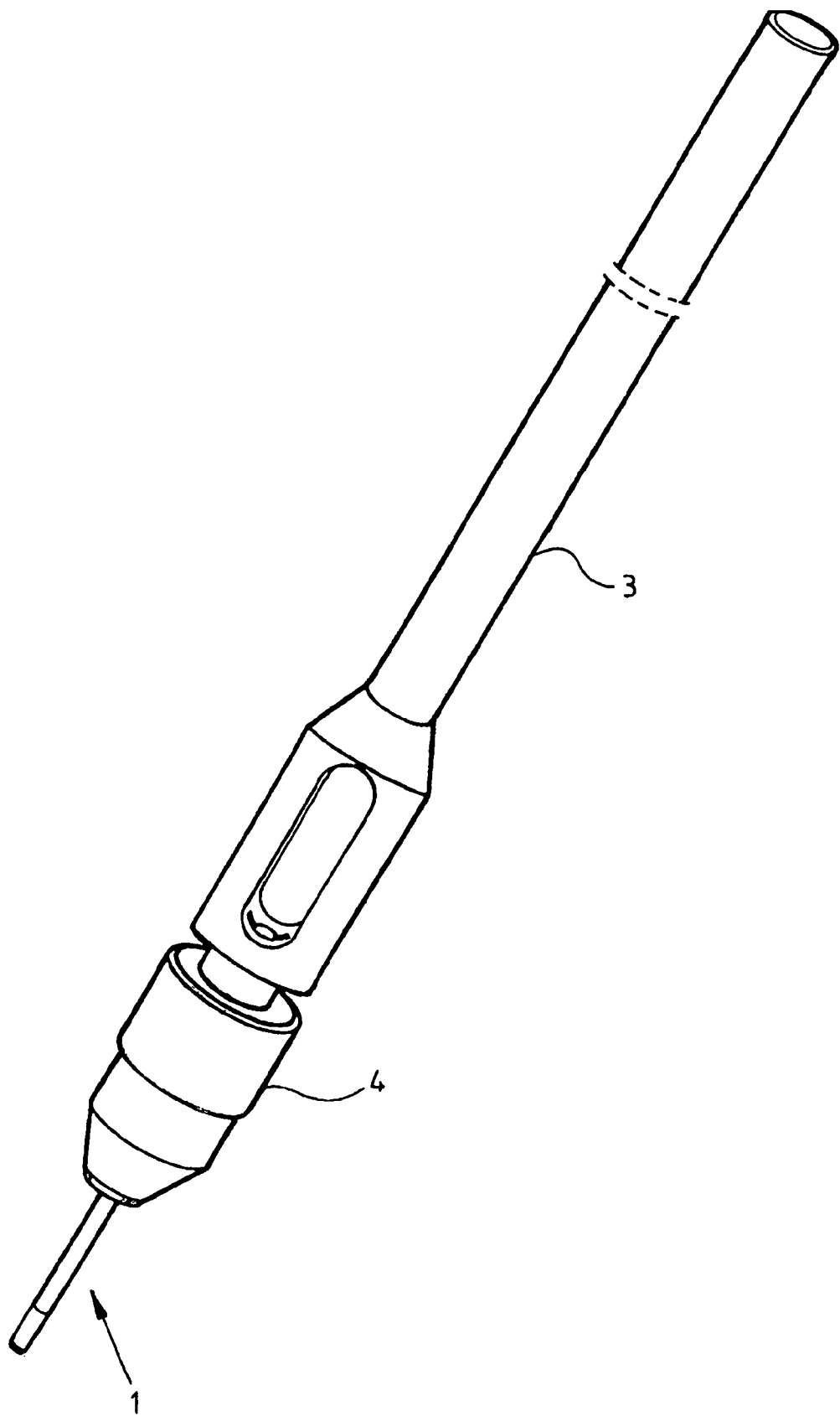
FIG. 1 shows a typical cutting head mounted at the choke of a shank adapted to perform hair harvesting operations.
Figure 2C:
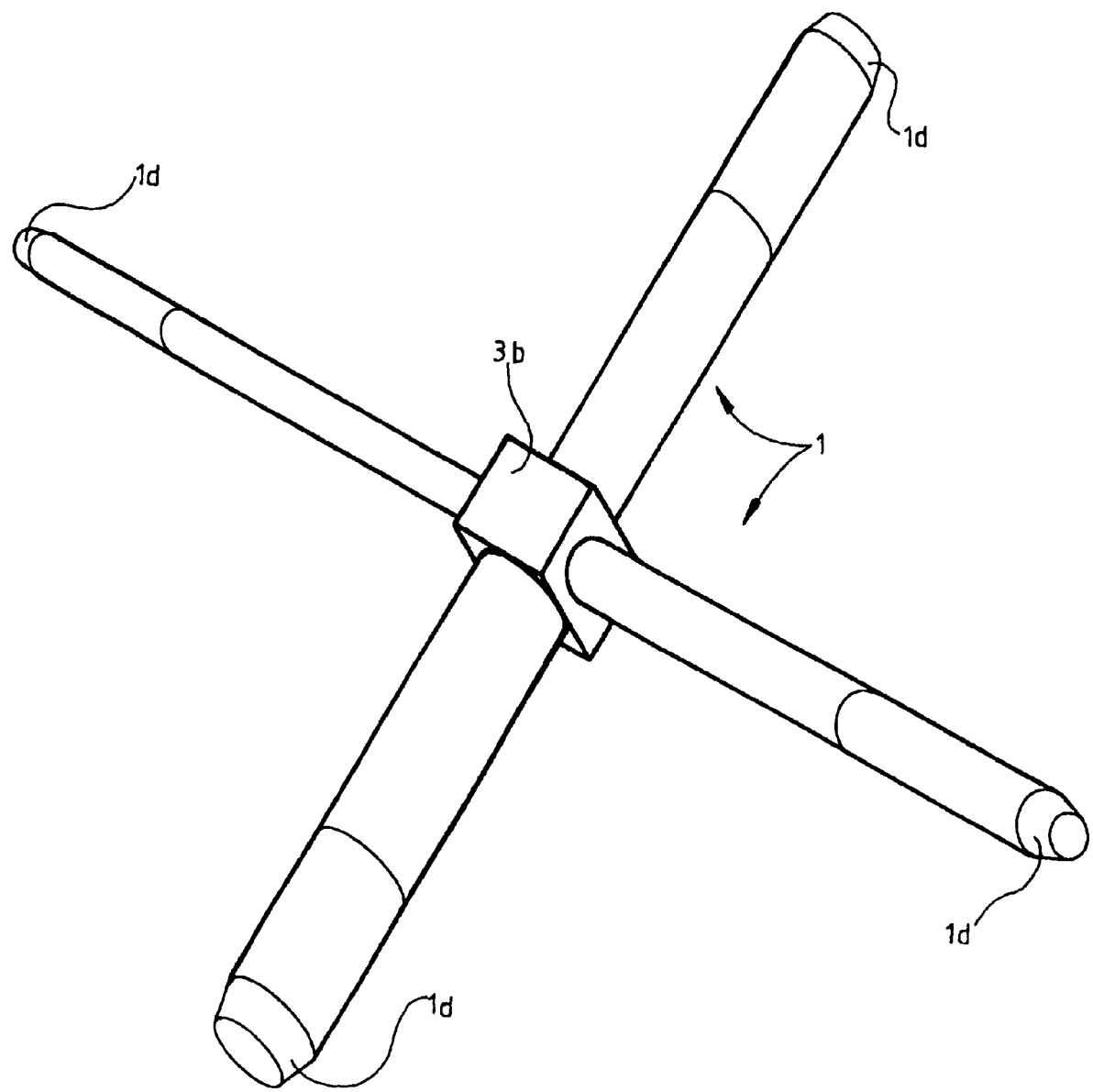
FIG. 2c illustrates a cross-like pattern of tubular cutting heads of varying diameters adapted to perform hair harvesting operations with hair follicles of varying anatomical characteristics.

FIGS. 1, 2a-2c show alternative illustrative embodiments of a hair harvesting device employed in the invention. The hair harvesting device is a tubular cutting head 1 that is divided along circumferential line 1c in a frontal part 1a and a rear part 1b, wherein the frontal part 1a is provided with an appropriate coating, gold or equivalent, to provide for a medically acceptable contact with the human body. Whilst a handle means for the tubular cutting head 1 is not necessary, a handle means is preferably used to facilitate the process and, if this is the case, the rear part 1b of the tubular cutting head 1 is appropriately connected at the frontal end of a handle means. The handle means is either a cylindrical shank 3 bearing a choke means 4 at the free end thereof wherein is being mounted the hair harvesting tubular cutting head 1 as depicted in FIG. 1 or it may alternatively be a plastic tubular shank 3a of appropriate length adapted to receive the tubular cutting head 1 at the free end thereof (FIG. 2a).

The frontal end 1a of the tubular cutting head 1 is formed with a conical knife edge cutting surface 1d adapted to successively perform cutting of single hair follicles when it is brought in contact with the root of the hair follicle and is manually rotated around the perimeter of the same.

In accordance to a preferred embodiment of the invention, as illustratively depicted in FIG. 2b, a pair of distinctly sized conical knife edge cutting surfaces 1d may be formed at both ends of a single tubular cutting head 1 or two tubular cutting heads with distinctly sized conical knife edge cutting surfaces may be mounted at two ends of a plastic cylindrical handle means, thereby serving the purpose of removal of single hair follicles of two alternative diameters by using one or the other knife edge cutting surface.

FIG. 2c presents yet another illustrative preferred embodiment of the invention wherein a cross like pattern of tubular cutting heads 1 extends outwardly from a centrally located shank 3b, each tubular cutting head 1 and accordingly each cutting edge thereof being provided with a different diameter, thereby rendering a multi-harvesting instrument capable of effecting removal of hair follicles of varying diameters.

The capacity of harvesting single hair follicles of varying diameters with the multi-dimensioned hair harvesting instruments described herein above is important in implementing the direct hair implantation process of the invention, since it allows rapid harvesting of hair follicles from various parts of the body that would otherwise necessitate the use of a plurality of hair harvesting instruments and the selection of this one having the appropriate diameter corresponding to the requirements of each particular hair follicle. Further, the capacity of harvesting hair follicles from a variety of locations of the human body appropriately allows obtaining hair follicles out of thicker hair follicles that may henceforth be divided to provide for more hair follicles, some of which may be implanted back into the donor region, thereby contributing towards effecting minimization of the hair diminishing picture of the same. The diameter of the knife edge cutting surface 1d of the tubular cutting head 1 of the invention may vary within a range of 0.40-2.00 mm to provide for hair harvesting operations in the overall hairy geography of the human body.

Following hair harvesting, a hair implanting device is used to effect placement of the hair follicles extracted from the donor region into selected loci of the recipient zone.

Figures 3A, 3B:
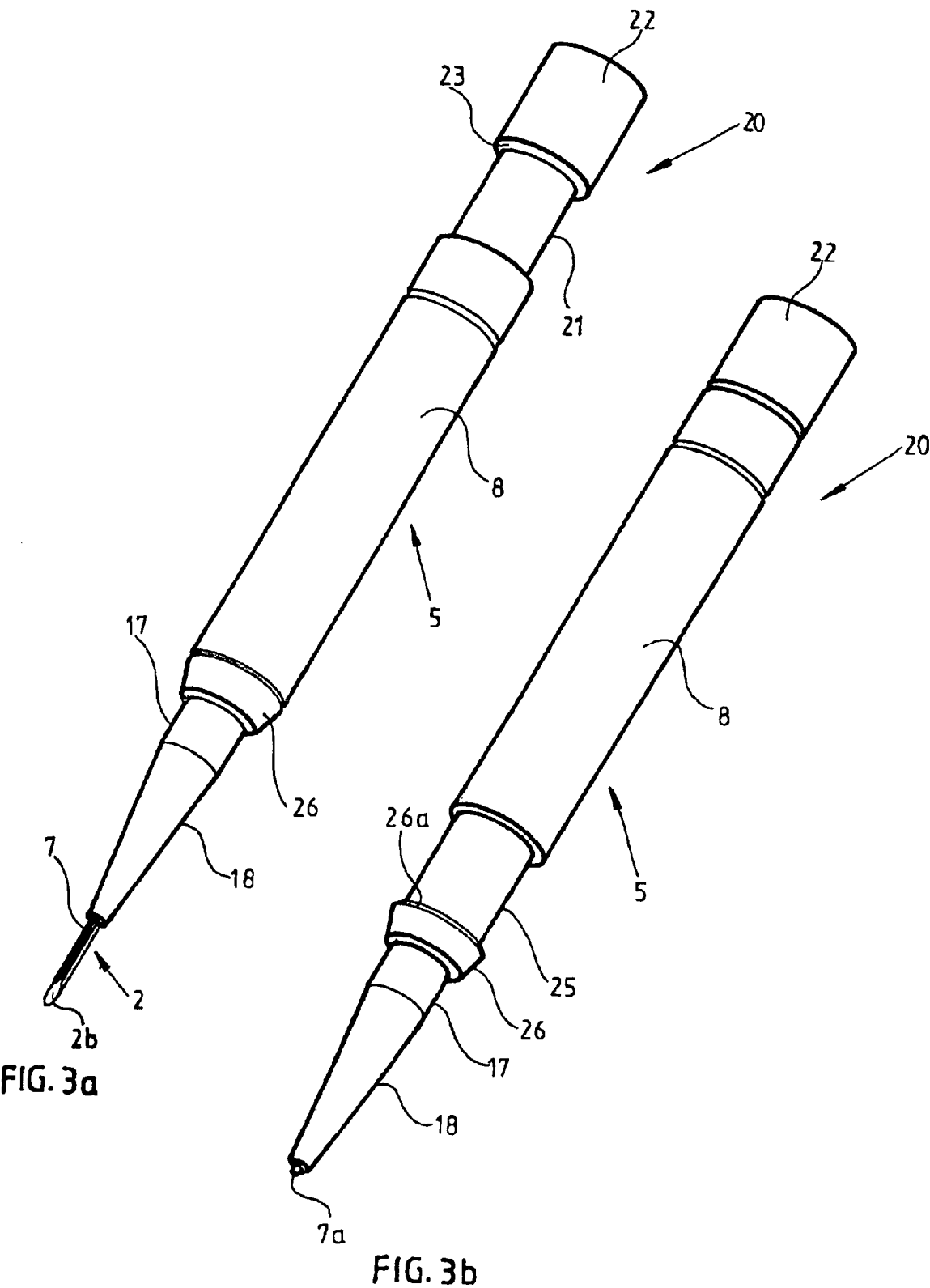
FIGS. 3a and 3b present a view in perspective of the hair implanting device with the needle respectively projected and retracted through the frontal end thereof.
Figure 3C:
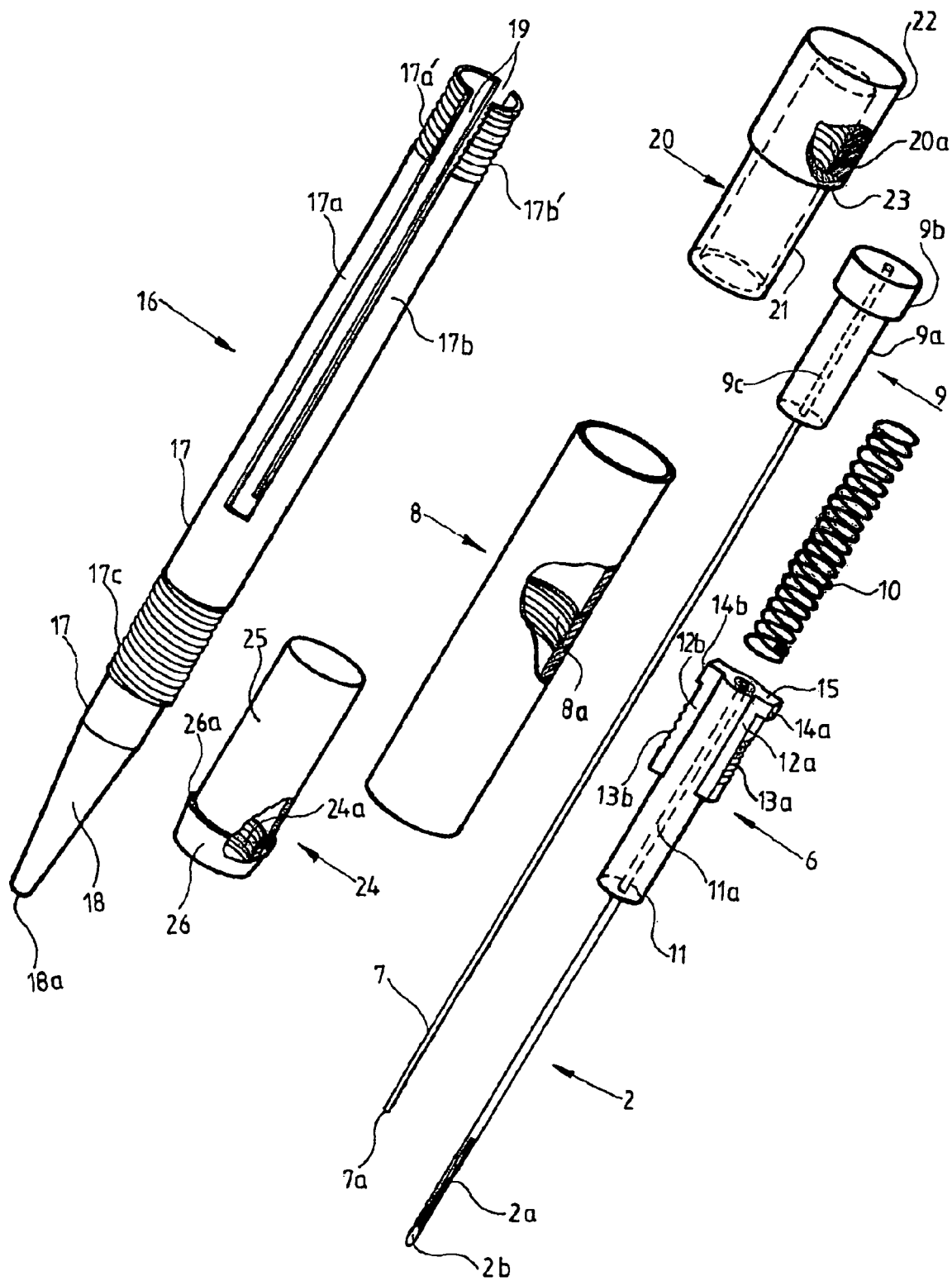
FIG. 3c presents a perspective exploded view of the hair implanting device depicted in FIGS. 3a, 3b.

In accordance with a first preferred embodiment of the invention a manually operated hair implanting device 5 is shown in FIGS. 3a, 3b, 3c. The hair implanting device 5 comprises a longitudinal hollow needle 2 with a holder means 6 and a push rod 7 with a holder means 9, wherein needle 2 is provided with a longitudinal groove 2a being formed at a frontal portion thereof with an obliquely cut free end 2b, wherein longitudinal groove 2a is adapted to receive a follicular hair unit and wherein push rod 7 is reciprocatingly movable axially along the interior of needle 2 to effect placement of the follicular hair unit disposed within the groove 2a of the frontal end of the needle at a selected position of the scalp at the recipient bald area.

The hair implanting device 5 further comprises a tubular housing made up from a plurality of various parts adapted to receive needle 2 and sliding push rod 7 and incorporating means of performing the hair implanting operation and means of preferentially regulating and fine adjustment of the depth of intrusion of the needle into the scalp to provide for optimum performance of the hair implanting device.

Assembly of the operating part of the hair implanting device 5 is advantageously implemented using a centrally located cylindrical plastic housing 8 open at both ends thereof, wherein housing 8 comprises a threaded section 8a within a small portion of the internal perimeter thereof. The holder means 6 of needle 2 comprises a hollow shaft with a through central hole 11a wherein needle 2 is being fitted. The hollow shaft of the holder means 6 comprises a frontal cylindrical portion 11 and a rear continuing cylindrical portion provided with lateral flanges 12a, 12b constituting equivalent sectors of a circular section, located at diametrically opposite sides of the continuing frontal cylindrical portion 11, wherein, flanges 12a, 12b are appropriately externally threaded with threading provisions 13a, 13b respectively, so as to allow screwing into the internally threaded section 8a of the centrally located cylindrical housing 8 and thereby fixedly mounting holder means 6 therein. The upper parts of lateral flanges 12a, 12b extend to projected ends 14a, 14b that fit in firm contact with the interior walls of cylindrical housing 8 at a region past the internally threaded section 8a. Needle holder means 6 is finally provided with an upper rear surface 15 whereupon sits one end of a spirally formed spring means 10.

The holder means 9 of the push rod 7 is a cylindrical plastic housing comprising a through hole 9c axially along the body thereof wherein fits the push rod 7. The cylindrical plastic housing 9 comprises a frontal portion 9a and a rear portion 9b, the latter having a marginally larger diameter so as to comprise a terminal basement of a longitudinal plastic housing 16 to be described hereinbelow.

Assembly of the needle-push rod arrangement is performed with needle 2 being inserted within holder means 6, holder means 6 being inserted within centrally located cylindrical housing 8 through a frontal open end thereof and fixedly screwed therein, push rod 7 being inserted within holder means 9, spirally formed spring means 10 being mounted around push rod 7 with one end thereof sitting onto the frontal circular basement end of portion 9a and the assembly of the push rod 7 surrounded by spring means 10 being inserted within the centrally located cylindrical housing 8 through the rear open end thereof, whereby the free end of spring means 10 sits onto the upper rear surface 15 of needle holder means 6 whilst push rod 7 appropriately passes through hole 11a within the interior of tubular needle 2.

Following assembly of the needle and push rod assembly within cylindrical housing 8, a longitudinal plastic housing 16 is guided within centrally located plastic housing 8 to integrate the entire assembly in combination with a rear push button portion 20. Longitudinal plastic housing 16 is a hollow cylindrical unit 17 with a frontal conical portion 18 and a rear portion that is longitudinally cut so as to remove two diametrically opposite sectors thereof and form diametrically opposite channels 19 and a pair of nearly semicircular identical portions 17a, 17b, that appropriately have a length equivalent to that of the centrally located housing 8.

The frontal conical portion 18 ends at an open end 18a through which extends the needle and push rod assembly during the hair implantation process. The rear end of each one of the pair of nearly semicircular identical portions 17a, 17b of longitudinal plastic housing 16 is provided with an externally threaded region 17a', 17b', whilst the frontal end of cylindrical unit 17 prior to the frontal conical portion 18 thereof comprises a further externally threaded region 17c.

The rear push button portion 20 is a plastic hollow cylindrical housing with a first portion 21 and a second portion 22, wherein second portion 22 has a diameter marginally larger than the diameter of the first portion 21 so as to externally form a circumferential basement 23 that acts as a terminal means of the push button operation when it touches onto the rim of the rear open end of centrally located housing 8 whilst the first portion 21 thereof has been inserted within the latter.

The longitudinal plastic portion 16 passes through the centrally located cylindrical housing 8 into the cylindrical housing of the rear push button portion 20 wherein the externally threaded portions 17a', 17b' of the corresponding pair of portions 17a, 17b are screwed within the internal threading 20a of portion 20. It is noted that longitudinally cut channels 19 appropriately allow passage of longitudinal housing 16 through the end protrusions 14a, 14b of holder means 6 that have previously been fixedly fitted onto the interior walls of housing 8. In this respect channels 19 are sized accordingly so as to allow free passage of end protrusions 14a, 14b in between them.

As shown in FIG. 3c, following assembly of the manually operated hair implanting device, a further plastic item 24 is employed to provide advantageous regulation of the length of the needle 2 protruding through the frontal outlet 18a of the device, thereby regulating depth of intrusion of needle 2 into the scalp in accordance with requirements in each individual hair implantation process. Plastic item 24 is a cylindrical housing open at both ends thereof comprising a main cylindrical portion 25 that fits around longitudinal housing portion 16 and within the centrally located cylindrical housing 8 and an end portion 26 the interior of which comprises threading 24a appropriate for screwing item 24 onto the frontal external threading 17c of the longitudinal housing portion 16, whilst its exterior is conically formed so as to create a rim 26a that serves as a terminal of the insertion of item 24 through the frontal end of the centrally located cylindrical housing 8. Since needle 2 is fixedly mounted within the centrally located cylindrical housing 8, the movement of plastic item 24 through differentiated screwing thereof along the stroke determined by the length of external threading 17c of longitudinal housing portion 16 results in a corresponding differentiated protrusion of needle 2 through the frontal outlet 18a of conically formed frontal end portion 18 of the longitudinal housing portion 16.

It is hereby noted that hollow needle 2 comprises a frontal portion 2a in which a sector has been removed so as to form a concave receiving section wherein is mounted the follicular hair unit to be implanted, whilst the frontal end 2b thereof is obliquely cut to form an appropriate configuration for intrusion into the scalp.

Whilst FIGS. 4a and 4b present detailed views of a hair harvesting and of a hair implanting device respectively, in accordance with a preferred embodiment of the invention, as depicted in the detailed views of FIG. 4c and FIG. 4d, the hair harvesting and hair implanting device are combined into a single hair transplanting device, whereby the tubular cutting head 1 of the independent hair harvesting device also serves as the follicle implanting needle 2 of the hair implanting device. In this embodiment the frontal end of the combined cutting head and implanting needle member is again appropriately obliquely cut so as to form the hair follicle receiving frontal cavity 2b of the implanting needle of the independent hair implanting device and at the same time it is conically sharpened so as to form the necessary conical knife edge cutting surface 1d of the independent hair harvesting device. Push rod 7 is again reciprocatingly movable within the tubular member 1, 2 to push the hair follicle into the recipient locus of the scalp. Combined tubular cutting head and implanting needle member 1, 2 does not now need to comprise the frontal longitudinally cut channel 2a that serves to form an appropriate hair follicle receiving cavity, since employing this combined double role device, each hair follicle can be implanted into the recipient zone immediately after removal thereof, thereby minimizing possibilities of the hair follicle being damaged due to extended staying thereof disconnected from living tissue. A longitudinal window 27 (FIG. 4d) might however be provided along this combined cutting head-implanting needle member to allow visual inspection of hair follicles being located within tubular member 1, 2.

In accordance with a preferred embodiment of the invention, as illustrated in the cross-sectional views of either FIG. 4c or FIG. 4d, the frontal end 1d, 2b of the combined cutting head-implanting needle member 1, 2 comprises inwardly cut sharpened surfaces instead of the outwardly exterior cut sharpened surfaces of the hair harvesting device as illustrated in the cross sectional view of FIG. 4a.

Figure 5A:
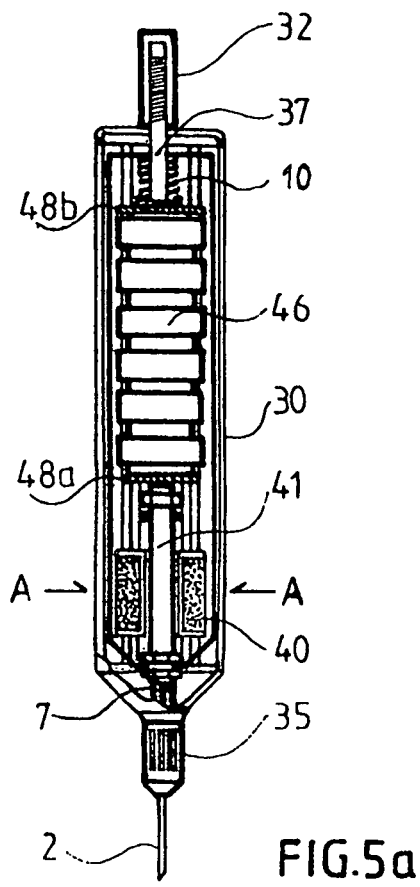
FIGS. 5a, 5b respectively show a longitudinal and a transversal cross-sectional view A-A of the electrically operated hair transplanting device of FIG. 5.
Figure 5:
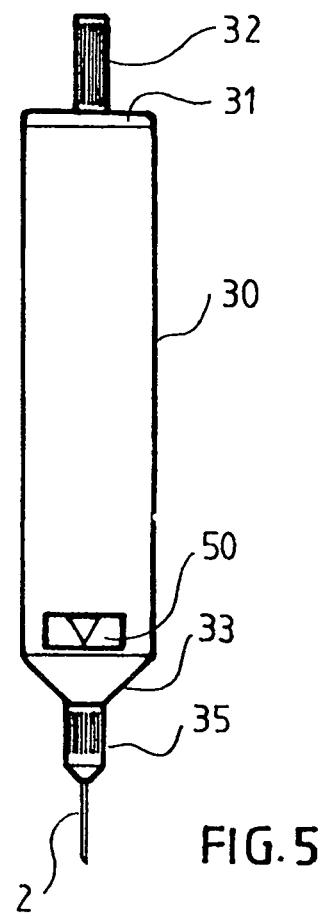
FIG. 5 presents a frontal view of an electrically operated hair transplanting device.

FIG. 5 illustrates an alternative electrically operated hair transplanting device that comprises a tubular housing 30 open at both ends thereof provided with a rear plug means 31 and tubular shaft 32 receiving a retraction activating spring 10 and a frontal conically formed extension 33 with a tubular shaft 35 receiving the forwardly projecting needle 2 that effects a hair implanting procedure of a hair follicle mounted within the concave cavity 2a thereof through pressing button means 50 provided onto the tubular housing 30 that initiates a forward stroke of push rod 7 slidable within the interior of needle 2.

Figure 5B:
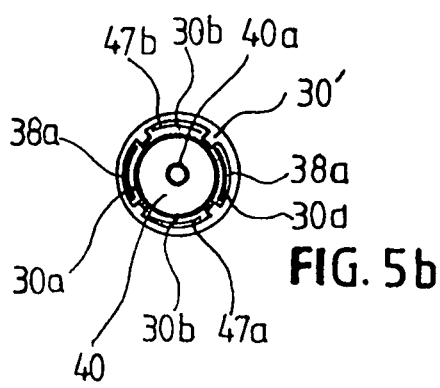

The cross sectional view of the tubular housing 30 shown in FIG. 5b illustrates the structure of the interior of tubular housing 30 that comprises longitudinally extending protruding nerves 30' that form a cross like pattern of two pairs of diametrically opposite channels 30a and 30b. A metallic frame 38 formed with a pair of longitudinally extending parallel sides 38a connected with an upper side 38b and a conically formed lower side 38c is appropriately fitted into tubular housing 30 with its longitudinally extending parallel sides 38a restrained within the pair of opposite channels 30a.

Figure 5C:
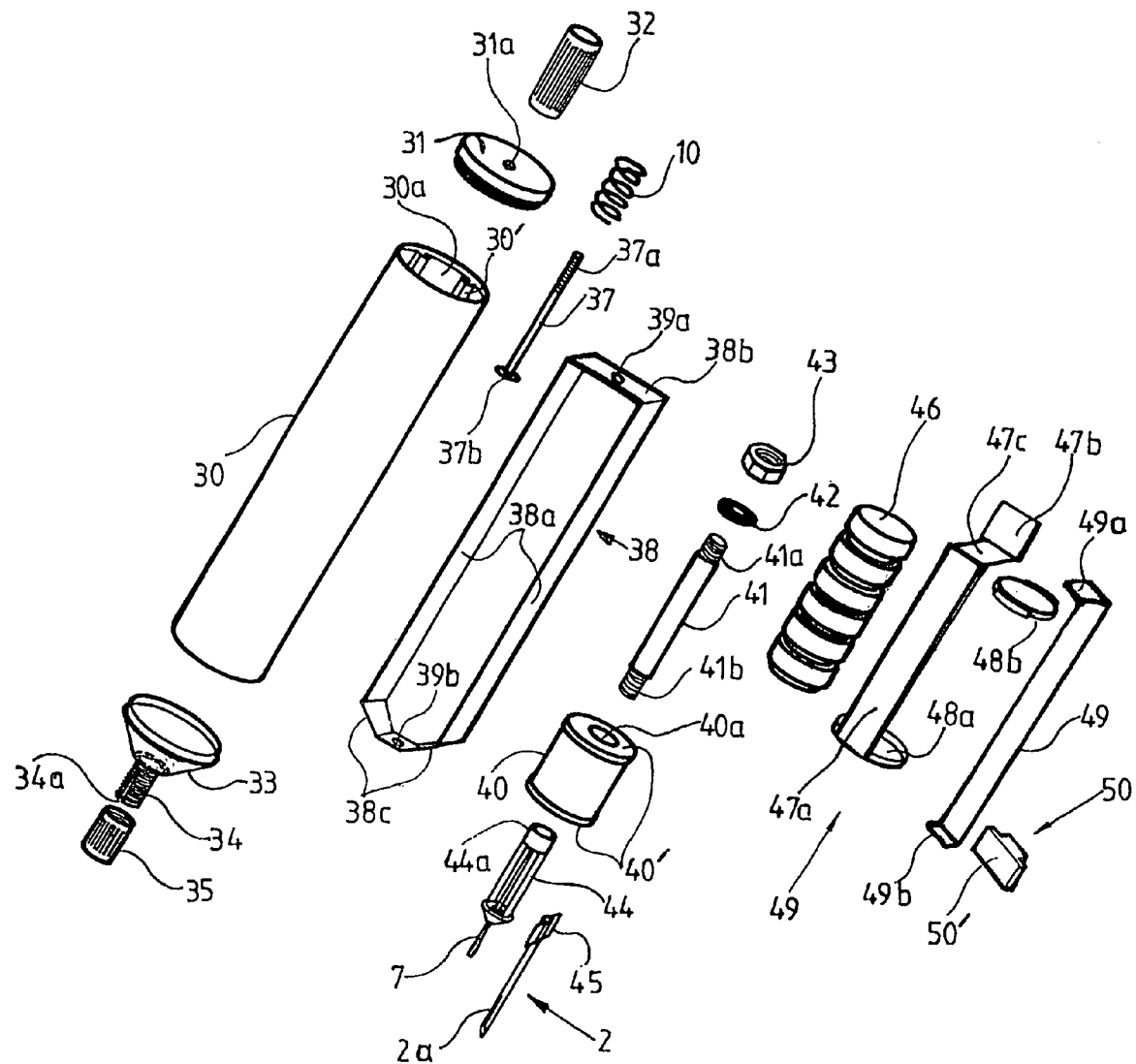
FIG. 5c shows an exploded view of the electrically operated hair transplanting device of FIG. 5.

As shown in the detailed exploded view of FIG. 5c, the electrically operated hair transplanting device comprises a battery assembly 46 that is attached in between opposing legs 48a and 47c of a metallic bridge 49 comprising a member 47a with a length equivalent to the length of battery 46 that extends at a bottom pole contacting leg 48a and an upper pole contacting leg 47c wherein is attached a plastic washer 48b to constitute the upper pole contacting leg of the battery. Leg 47c extends into an upwardly extending flange 47b, such that the overall metallic bridge construction may be mounted with member 47a and parallel extension 47b within the other pair of opposite channels 30b in the interior of tubular housing 30.

A cylindrical magnetic core 40 with a through hole 40a is provided with a reciprocating piston 41 that passes through hole 40a and is provided with threaded portions 41a and 41b at the two ends thereof. An elastic washer 42 and nut 43 is screwed at the upper threaded portion 41a of piston 41 providing safe contact with the magnetic core 40, whilst the other threaded end 41b of piston 41 is screwed within an interior threaded opening 44a of needle pushing rod holder means 44, after having passed through opening 39b at the bottom of the metallic frame structure 38 whereupon it has been fixedly mounted.

The needle and push rod assembly of the hair transplanting device is appropriately mounted within a frontal conically formed extension 33 that is formed so as to detachably fit into the bottom open end of tubular housing 30. Push rod 7 is fitted within a cylindrical structure 44 that is mounted within the cavity of the frontal conically formed extension 33 so that push rod 7 may pass through an underlying cylindrical member 34 of the conically formed extension 33 into the hollow interior of needle 2 that is provided with suspending blade extensions 45 that clip into appropriately cut channels 34a at the exterior of cylindrical member 34. Eventually an internally threaded cylindrical plug means 35 is screwed around the externally threaded perimeter of cylindrical member 34. It is hereby noted that differentiated protrusion of needle 2 through the frontal outlet of the hair transplanting device is obtained through differentiated depth of screwing of the internally threaded tubular shaft 35 around the externally threaded perimeter of the cylindrical member 34.

An elongated bolt 37 is employed to fixedly connect the upper end of metallic frame structure 38 to the rear plug means 32. Bolt 37 is provided with a frontal threaded portion 37a that is screwed within the internally threaded cylindrical extension 32 after having passed through hole 39a of the metallic frame structure 38 and through centrally located hole 31a of the upper plug means 31 sealing the open end of tubular housing 30. Spring means 10 is spirally wound around elongated bolt 37 being restrained in between the upper pole 48b of the battery 46 and the upper wall 38b of the metallic frame structure 38.

During a hair implanting operation with the electrically operated device of FIGS. 5, 5a-5c, a downward stroke of push rod 7 effecting unloading into the recipient locus of the scalp of the hair follicle loaded within concave frontal cavity 2a of needle 2 is initiated when push button 50 is pressed, whereby the interior surface 50' of button 50 exerts pressure onto metallic leg extension 49b of a metallic foil 49 that contacts metallised bottom surface 40' of magnetic core 40, thereby effecting magnetization of core 40, which results in activating a downward stroke of piston rod 41 and accordingly of push rod 7 together with the entire metallic frame structure 38 with which it is fixedly connected. As frame structure 38 moves downwardly, spring 10 is being compressed and when following conclusion of hair implanting operation button 50 is released, the electric circuit is interrupted and the metallic frame structure 38 returns at rest position through mechanical unloading action of spring means 10.

In accordance with a preferred embodiment of the invention the electrically operated hair transplanting device described hereinabove can be advantageously utilized to perform a hair harvesting operation accordingly with a needle design similar to that depicted in FIG. 4c or 4d. If this is the case the hair harvesting operation is conducted manually with a rotating movement of the projected end of the cutting head-needle implanting member, whilst implanting is henceforth performed electrically through operation of button means 50.

It is hereby noted that any changes or amendments in the above that do not constitute a new inventive step are considered part of the scope and aims of the present invention as defined in the claims.

The invention claimed is:

1. A hair transplanting device comprising hair harvesting means and hair implanting means adapted to perform sequential removal of single hair follicles from a donor region and implantation of the same at a recipient zone of the scalp, said hair harvesting means comprising a tubular cutting head (1) with a frontal end (1a) bearing a conical knife edge cutting surface (1d) adapted to successively perform cutting of single hair follicles when brought in contact with the root of the hair follicle and manually rotated around the perimeter of the same and said hair implanting means comprising a hollow needle (2), a longitudinal groove (2a) being formed at a frontal portion of needle (2) with an obliquely cut free end (2b) adapted to receive a follicular hair unit, a push rod (7) being reciprocatingly movable axially along the interior of said hollow needle to effect placement of the follicular hair unit disposed within the groove (2a) of the frontal end of the needle within a predetermined position at the recipient zone of the scalp, and compression means adapted to activate a forward movement of said push rod (7) axially along the interior of said needle (2) and return spring means (10) adapted to activate a rearward movement of said push rod (7) back to rest position following conclusion of a single hair follicle implanting operation, characterized in that said hair harvesting means comprises a plurality of tubular cutting heads (1), each tubular cutting head (1) with at least one or a pair of distinctly sized conical knife edge cutting surfaces (1d) provided at the ends thereof, said plurality of tubular cutting heads (1) with distinctly sized conical knife edge cutting surfaces (1d) being mounted at a single plastic cylindrical handle means, said single plastic cylindrical handle means being used to remove single hair follicles of alternative diameters by successively bringing into position of usage one appropriate cutting surface (1d) of said plurality of tubular cutting heads (1) with at least one or a pair of distinctly sized conical knife edge cutting surfaces (1d), and in that said hair implanting means comprises means of appropriately regulating and finely adjusting of the depth of intrusion of said needle (2) into the scalp to provide for optimum performance of the hair implanting operation, and in that the hair transplanting device is adapted to function electrically with said compression means, said compression means adapted to activate a forward movement of said push rod (7) axially along the interior of said needle (2) via a press button means (50), the hair transplanting device further comprising a tubular housing (30) open at both ends thereof provided with a rear plug means (31) extending at a tubular shaft (32) and a frontal conically formed extension (33) with a second tubular shaft (35) receiving the forwardly projecting needle (2) that effects a hair implanting procedure of a hair follicle mounted within the longitudinal groove (2a) thereof, wherein a hair implanting operation is initiated through pressing button means (50) provided onto said tubular housing (30) that activates a forward stroke of push rod (7) slidable within the interior of needle (2), said tubular housing (30) comprising longitudinally extending protruding nerves (30) forming a cross like pattern of two pairs of diametrically opposite channels (30a, 30b), a metallic frame (38) formed with a pair of longitudinally extending parallel sides (38a) joined with a linear upper side (38b) and a conically formed lower side (38c) being fitted within said tubular housing (30) with said longitudinally extending parallel sides (38a) restrained within said pair of diametrically opposite channels (30a), a battery assembly (46) comprising a metallic bridge (49) with a member (47a) extending at a length equivalent to the length of said battery assembly (46), a bottom pole contacting leg (48a) and an upper pole contacting leg (47c) extending into an upwardly extending flange (47b), said battery assembly (46) and metallic bridge (49) thereof being mounted within said pair of diametrically opposite channels (30b) of said tubular housing (30), a cylindrical magnetic core (40) with a through hole (40a) being provided at the bottom of said metallic frame (38), a reciprocating piston (41) passing through said hole (40a) of said magnetic core (40), an upper threaded end (41a) of said piston (41) being screwed with a nut (43) and a lower threaded end (41b) of said piston (41) being screwed within an interior threaded opening (44a) of said needle pushing rod (7) holder means (44) passing through an opening (39b) at the bottom of said metallic frame structure (38), said needle and push rod assembly of the hair implanting device being appropriately mounted within said frontal conically formed extension (33) detachably fitted into the bottom open end of tubular housing (30), a cylindrical member (34) extending underneath said conically formed extension (33), said cylindrical member (34) being provided with an arrangement of appropriately cut channels (34a) at the exterior thereof, said needle (2) being provided with suspending blade extensions (45) fixedly fitted within said channels (34a) of said cylindrical member (34), wherein said means of appropriately regulating and finely adjusting of the depth of intrusion of said needle (2) into the scalp is said second tubular shaft (35), whereby differentiated protrusion of said needle (2) through the frontal end of said hair transplanting device is obtained through differentiated depth of screwing of the internally threaded second tubular shaft (35) around the externally threaded perimeter of said cylindrical member (34).

2. The hair transplanting device of claim 1, characterized in that said frontal portion of said needle (2) of said hair implanting means that is appropriately obliquely cut so as to form a hair follicle receiving frontal cavity (2b) is at the same time conically sharpened so as to form the necessary conical knife edge cutting surface (1d) of said hair harvesting means, whereby a single hair transplanting means is provided capable of performing both hair harvesting and hair implanting operations.

3. The hair transplanting device of claim 2, characterized in that said frontal end of needle (2) that is conically sharpened to provide for hair harvesting capacity comprises inwardly cut sharpened surfaces.

4. The hair transplanting device of claim 1 characterized in that said return spring means (10) adapted to activate a rearward movement of said push rod (7) back to rest position following conclusion of a single hair follicle implanting operation is spirally wound around an elongated bolt (37) mounted so as to fixedly connect the upper end of said metallic frame (38) to said rear plug means (32), said elongated bolt (37) being provided with a frontal threaded portion (37a) that is screwed within the internally threaded said tubular shaft (32) after having passed through an upper hole (39a) of said metallic frame structure (38) and through a centrally located hole (31a) of said rear plug means (31), said elongated bolt (37) being restrained in between an upper pole (48b) of said battery assembly (46) and said upper side (38b) of said metallic frame (38).

5. A method of sequentially harvesting single hair follicles from a donor region and implanting the same at a recipient region of the scalp using the hair transplanting device of claim 1, said method characterized in that it comprises in combination the steps of:

appropriately regulating and finely adjusting the depth of intrusion of a forwardly projecting tubular needle of the hair transplanting device into the scalp to provide for optimum performance of the hair transplanting operation;

placing said hair transplanting device, provided with said forwardly projecting tubular needle with an outermost end being formed with a conical obliquely cut knife edge cutting surface, at a target donor region of the scalp and rotating said conical obliquely cut knife edge cutting surface of said tubular needle around a selected hair follicle thereby cutting the scalp about the selected hair follicle and extracting said hair follicle;

withholding said extracted hair follicle within said conical obliquely cut surface of said forwardly projecting tubular needle, positioning said projected needle portion at a target recipient locus of the scalp and effecting a hair implanting operation of the hair follicle mounted within the obliquely cut surface of said forwardly projecting tubular needle through pressing a button means provided onto a tubular housing of the hair transplanting device thereby initiating a forward stroke of a push rod slidable within the interior of said tubular needle to implant said hair follicle into said target recipient locus of the scalp, wherein a spring means axially disposed along the axis of the stroke of said push rod is being compressed and loaded during said forward stroke of said push rod and is subsequently unloaded thereby returning said forwardly projecting tubular needle at rest position for performing another hair follicle extracting and implanting operation.

\* \* \* \* \*